United States Patent
Dechelette et al.

(10) Patent No.: US 11,033,676 B2
(45) Date of Patent: Jun. 15, 2021

(54) DRUG DELIVERY DEVICE AND METHOD FOR CONNECTING A FLUID FLOWPATH

(71) Applicant: UNL Holdings LLC, New York, NY (US)

(72) Inventors: Alexis Marie Adolphe Dechelette, Lancaster, PA (US); Robert S. Russo, Gettysburg, PA (US); Lawton Laurence, Phoenixville, PA (US); Shaun R. Devitt, Wayne, PA (US)

(73) Assignee: UNL Holdings LLC, New York, NY (US)

( * ) Notice: Subject to any disclaimer, the term of this patent is extended or adjusted under 35 U.S.C. 154(b) by 138 days.

(21) Appl. No.: 16/323,711

(22) PCT Filed: Aug. 8, 2017

(86) PCT No.: PCT/IB2017/000937
§ 371 (c)(1),
(2) Date: Feb. 6, 2019

(87) PCT Pub. No.: WO2018/029520
PCT Pub. Date: Feb. 15, 2018

(65) Prior Publication Data
US 2019/0167895 A1 Jun. 6, 2019

Related U.S. Application Data

(60) Provisional application No. 62/372,167, filed on Aug. 8, 2016, provisional application No. 62/412,532, filed on Oct. 25, 2016.

(51) Int. Cl.
*A61M 5/162* (2006.01)
*A61M 5/142* (2006.01)
(Continued)

(52) U.S. Cl.
CPC ........ *A61M 5/14248* (2013.01); *A61M 5/142* (2013.01); *A61M 5/1452* (2013.01);
(Continued)

(58) Field of Classification Search
CPC .. A61M 2005/1581; A61M 2039/0036; A61M 2039/0081; A61M 2039/205; A61M 39/00; A61M 5/142; A61M 5/162
See application file for complete search history.

(56) References Cited

U.S. PATENT DOCUMENTS 3,336,924 A   8/1967  Sarnoff et al.
3,401,692 A   9/1968  Harris, Jr.
(Continued)

FOREIGN PATENT DOCUMENTS

CN   101557847 A   10/2009
CN   101631585 A   1/2010
(Continued)

OTHER PUBLICATIONS

U.S. Food and Drug Administration, "Infusion Pump Improvement Initiative," Apr. 2010 (6 pages).
(Continued)

*Primary Examiner* — Deanna K Hall
(74) *Attorney, Agent, or Firm* — Hamilton, Brook, Smith & Reynolds, P.C.

(57) ABSTRACT

Provided herein is a fluid pathway connection assembly, e.g., for connecting a fluid flowpath within a drug delivery device for delivery of a medicament to a target site. The fluid pathway connection assembly comprises a hollow needle piercing member, a sleeve fixedly engaged with the piercing member and a pierceable seal configured to sealingly engage the piercing member or the sleeve. Upon, sealing engagement, the piercing member or the sleeve and the pierceable seal form a volume within which a portion of the piercing
(Continued)

member is disposed. The fluid pathway connection assembly is activated by relative movement between the piercing member and the pierceable seal and activation causes the piercing member to pierce the pierceable seal, thereby establishing a fluid flowpath through the pierceable seal. Upon incorporation of the assembly into a sealed fluid flowpath, the volume is isolated from the environment and maintains the sterile condition of the portion of the piercing member disposed therein. Also provided herein are drug delivery pumps and methods of operating and assembling the assemblies and pumps described herein.

15 Claims, 6 Drawing Sheets

(51) Int. Cl.
  A61M 5/158 (2006.01)
  A61M 5/145 (2006.01)
  A61M 39/00 (2006.01)
(52) U.S. Cl.
  CPC ...... A61M 5/1454 (2013.01); A61M 5/14566 (2013.01); A61M 5/158 (2013.01); A61M 5/162 (2013.01); A61M 2005/14252 (2013.01); A61M 2005/14256 (2013.01); A61M 2005/1581 (2013.01); A61M 2039/0081 (2013.01); A61M 2205/13 (2013.01)

(56) References Cited

U.S. PATENT DOCUMENTS

| | | | |
|---|---|---|---|
| 3,413,974 | A | 12/1968 | Cohen |
| 3,940,003 | A | 2/1976 | Larson |
| 4,004,586 | A | 1/1977 | Christensen et al. |
| 4,048,997 | A | 9/1977 | Raghavachari et al. |
| 4,565,543 | A | 1/1986 | Bckkcring et al. |
| 4,673,400 | A | 6/1987 | Martin |
| 4,685,903 | A | 8/1987 | Cable et al. |
| 4,755,173 | A | 7/1988 | Konopka et al. |
| 4,840,620 | A | 6/1989 | Kobayashi et al. |
| 5,147,311 | A | 9/1992 | Pickhard |
| 5,167,816 | A | 12/1992 | Kruger |
| 5,616,132 | A | 4/1997 | Newman |
| 5,766,147 | A | 6/1998 | Sancoff et al. |
| 5,795,339 | A | 8/1998 | Erskine |
| 5,851,197 | A | 12/1998 | Marano et al. |
| 5,858,001 | A | 1/1999 | Tsals et al. |
| 6,022,339 | A | 2/2000 | Fowles et al. |
| 6,030,363 | A | 2/2000 | Kriesel |
| 6,248,093 | B1 | 6/2001 | Moberg |
| 6,368,314 | B1 | 4/2002 | Kipfer et al. |
| 6,699,218 | B2 | 3/2004 | Flaherty et al. |
| 7,063,684 | B2 | 6/2006 | Moberg |
| 7,250,037 | B2 | 7/2007 | Shermer et al. |
| D564,087 | S | 3/2008 | Yodfat et al. |
| D585,543 | S | 1/2009 | Yodfat et al. |
| 7,479,135 | B2 | 1/2009 | Richter et al. |
| D586,463 | S | 2/2009 | Evans et al. |
| 7,611,503 | B2 | 11/2009 | Spohn et al. |
| 7,780,636 | B2 | 8/2010 | Radmer et al. |
| 7,803,134 | B2 | 9/2010 | Sharifi et al. |
| D629,503 | S | 12/2010 | Caffey et al. |
| 7,846,132 | B2 | 12/2010 | Gravesen et al. |
| 7,879,010 | B2 | 2/2011 | Hunn et al. |
| 7,905,859 | B2 | 3/2011 | Bynum et al. |
| 7,927,306 | B2 | 4/2011 | Cross et al. |
| 7,967,795 | B1 | 6/2011 | Cabiri |
| 8,029,472 | B2 | 10/2011 | Leinsing et al. |
| 8,048,031 | B2 | 11/2011 | Shaw et al. |
| 8,152,771 | B2 | 4/2012 | Mogensen et al. |
| 8,157,769 | B2 | 4/2012 | Cabiri |
| 8,162,892 | B2 | 4/2012 | Mogensen et al. |
| 8,167,844 | B2 | 5/2012 | Dillard, III |
| 8,187,232 | B2 | 5/2012 | Chong et al. |
| D669,165 | S | 10/2012 | Estes et al. |
| 8,409,145 | B2 | 4/2013 | Raymond et al. |
| D684,685 | S | 6/2013 | Schneider et al. |
| D684,686 | S | 6/2013 | Cronenberg |
| D685,083 | S | 6/2013 | Schneider et al. |
| 8,591,465 | B2 | 11/2013 | Hommann |
| D709,183 | S | 7/2014 | Kemlein |
| 8,795,234 | B2 | 8/2014 | Kadamus et al. |
| 8,939,935 | B2 | 1/2015 | O'Connor et al. |
| D723,157 | S | 2/2015 | Clemente et al. |
| 9,005,169 | B2 | 4/2015 | Gravesen et al. |
| D745,142 | S | 12/2015 | O'Connor et al. |
| D752,442 | S | 3/2016 | O'Donahue |
| D768,288 | S | 10/2016 | O'Connor et al. |
| 9,463,280 | B2 | 10/2016 | Cabiri |
| 9,511,189 | B2 | 12/2016 | O'Connor et al. |
| D791,306 | S | 7/2017 | Clemente et al. |
| 9,707,335 | B2 | 7/2017 | Agard et al. |
| 9,707,337 | B2 | 7/2017 | O'Connor et al. |
| 9,802,030 | B2 | 10/2017 | Clemente et al. |
| 10,369,274 | B2 | 8/2019 | O'Connor et al. |
| 2003/0199816 | A1 | 10/2003 | Ramming |
| 2004/0092478 | A1 | 5/2004 | Flaherty |
| 2007/0010789 | A1 | 1/2007 | Peter et al. |
| 2007/0179444 | A1 | 8/2007 | Causcy et al. |
| 2008/0132842 | A1 | 6/2008 | Flaherty |
| 2008/0269683 | A1 | 10/2008 | Bikovsky |
| 2008/0269687 | A1 | 10/2008 | Chong et al. |
| 2008/0269713 | A1 | 10/2008 | Kavazov |
| 2009/0124979 | A1 | 5/2009 | Raymond et al. |
| 2009/0204077 | A1 | 8/2009 | Hasted et al. |
| 2009/0240240 | A1 | 9/2009 | Hines et al. |
| 2011/0098652 | A1 | 4/2011 | Hasted et al. |
| 2011/0160678 | A1 | 6/2011 | Chong et al. |
| 2011/0166509 | A1 | 7/2011 | Gross et al. |
| 2011/0270188 | A1 | 11/2011 | Caffey et al. |
| 2012/0035546 | A1 | 2/2012 | Cabiri |
| 2012/0096953 | A1 | 4/2012 | Bente, IV et al. |
| 2012/0123354 | A1 | 5/2012 | Woehr |
| 2012/0211946 | A1 | 8/2012 | Halili et al. |
| 2013/0060196 | A1 | 3/2013 | O'Connor et al. |
| 2013/0060233 | A1 | 3/2013 | O'Connor et al. |
| 2013/0066274 | A1 | 3/2013 | O'Connor et al. |
| 2013/0131595 | A1 | 5/2013 | Ekman et al. |
| 2014/0200510 | A1 | 7/2014 | Agard et al. |
| 2015/0141920 | A1 | 5/2015 | O'Connor et al. |
| 2015/0359965 | A1 | 12/2015 | O'Connor et al. |
| 2016/0199583 | A1 | 7/2016 | Tan-Malecki et al. |
| 2017/0080149 | A1 | 3/2017 | O'Connor et al. |
| 2017/0281859 | A1 | 10/2017 | Agard et al. |
| 2018/0008769 | A1 | 1/2018 | O'Connor et al. |
| 2019/0022306 | A1* | 1/2019 | Gibson ............ A61M 5/14566 |
| 2019/0358394 | A1 | 11/2019 | O'Connor et al. |

FOREIGN PATENT DOCUMENTS

| | | |
|---|---|---|
| EP | 0 589 328 A2 | 3/1994 |
| EP | 1039947 A1 | 6/2001 |
| EP | 1 219 283 A2 | 7/2002 |
| EP | 1 702 635 A2 | 9/2006 |
| EP | 1 341 569 B1 | 1/2007 |
| EP | 1 427 471 B1 | 2/2008 |
| EP | 1 695 727 B1 | 7/2008 |
| EP | 1 513 580 B1 | 3/2009 |
| EP | 2 077 128 A1 | 7/2009 |
| EP | 2 269 559 A2 | 1/2011 |
| EP | 2 379 134 A1 | 10/2011 |
| EP | 2 429 612 A1 | 3/2012 |
| EP | 2 433 663 A1 | 3/2012 |
| JP | S59-500600 A | 8/1983 |
| JP | H09-502116 A | 3/1997 |
| JP | 2000-189494 A | 7/2000 |
| JP | 2002-507459 A | 3/2002 |
| JP | 2002-524217 A | 8/2002 |
| JP | 2003-527159 A | 9/2003 |
| JP | 2004-195227 A | 7/2004 |
| JP | 2004-528939 A | 9/2004 |

(56) References Cited

FOREIGN PATENT DOCUMENTS

| | | |
|---|---|---|
| JP | 2010-501211 A | 1/2010 |
| JP | 2010-501281 A | 1/2010 |
| JP | 2010-528810 A | 8/2010 |
| JP | 2010-531196 A | 9/2010 |
| JP | 2010-538751 A | 12/2010 |
| JP | 2011-045537 A | 3/2011 |
| JP | 2011-511689 A | 4/2011 |
| WO | WO 1983/03540 A1 | 10/1983 |
| WO | WO 95/19194 A1 | 7/1995 |
| WO | WO 96/40327 A1 | 12/1996 |
| WO | WO 99/030768 A1 | 6/1999 |
| WO | WO 99/048546 A1 | 9/1999 |
| WO | WO 00/15292 A2 | 3/2000 |
| WO | WO 01/30424 A1 | 5/2001 |
| WO | WO 2003/024504 A2 | 3/2003 |
| WO | WO 2003/103763 A1 | 12/2003 |
| WO | WO 2004/035116 A1 | 4/2004 |
| WO | WO 2004/062714 A1 | 7/2004 |
| WO | WO 2005/002492 A1 | 1/2005 |
| WO | WO 2005/037350 A2 | 4/2005 |
| WO | WO 2005/044344 A1 | 5/2005 |
| WO | WO 2006/129196 A1 | 12/2006 |
| WO | WO 2008/024808 A2 | 2/2008 |
| WO | WO 2008/105954 A2 | 9/2008 |
| WO | WO 2008/133702 A1 | 11/2008 |
| WO | WO 2008/153460 A1 | 12/2008 |
| WO | WO 2009/101145 A1 | 8/2009 |
| WO | WO 2010/029054 A1 | 3/2010 |
| WO | WO 2010/077807 A1 | 7/2010 |
| WO | WO 2010/084113 A1 | 7/2010 |
| WO | WO 2010/085338 A1 | 7/2010 |
| WO | WO 2010/112377 A1 | 10/2010 |
| WO | WO 2010/132196 A1 | 11/2010 |
| WO | WO 2010/139672 A1 | 12/2010 |
| WO | WO 2011/006652 A1 | 1/2011 |
| WO | WO 2011/014514 A1 | 2/2011 |
| WO | WO 2011/046950 A1 | 4/2011 |
| WO | WO 2011/090956 A2 | 7/2011 |
| WO | WO 2011/121023 A1 | 10/2011 |
| WO | WO 2012/032411 A2 | 3/2012 |
| WO | WO 2012/131044 A1 | 10/2012 |
| WO | WO 2013/033467 A2 | 3/2013 |
| WO | WO 2013/040032 A1 | 3/2013 |
| WO | WO 2013/156224 A1 | 10/2013 |
| WO | WO 2014/11879 A2 | 1/2014 |
| WO | WO 2016/048878 A1 | 3/2016 |
| WO | WO 2016/049532 A1 | 3/2016 |
| WO | WO 2016/141082 A1 | 9/2016 |
| WO | WO 2018/029520 A1 | 2/2018 |

OTHER PUBLICATIONS

Meng et al., "MEMS-enabled implantable drug infusion pumps for laboratory animal research, preclinical, and clinical applications," *Adv. Drug. Deliv. Rev.*, 64(14): 1628-1638 (Nov. 2012).

International Preliminary Report on Patentability for International Application No. PCT/IB2017/000937, titled: "Drug Delivery Device and Method for Connecting a Fluid Flowpath," dated Feb. 12, 2019.

International Search Report for International Application No. PCTAB2017/000937, titled: "Drug Delivery Device and Method for Connecting a Fluid Flowpath," dated Nov. 14, 2017.

Written Opinion for International Application No. PCT/IB2017/000937, titled: "Drug Delivery Device and Method for Connecting a Fluid Flowpath," dated Nov. 14, 2017.

\* cited by examiner

DRUG DELIVERY DEVICE AND METHOD FOR CONNECTING A FLUID FLOWPATH

RELATED APPLICATIONS

This application is the U.S. National Stage of International Application No. PCT/IB2017/000937, filed Aug. 8, 2017, which designates the U.S., published in English, and claims the benefit of U.S. Provisional Application No. 62/372,167, filed on Aug. 8, 2016, and U.S. Provisional Application No. 62/412,532, filed on Oct. 25, 2016. The entire teachings of the above applications are incorporated herein by reference.

FIELD

This invention relates to connections for establishing a fluid flowpath. More particularly, this invention relates to devices and methods for connecting a fluid flowpath within a drug delivery device for delivery of a medicament to a target site.

BACKGROUND

Parenteral delivery of various drugs, i.e., delivery by means other than through the digestive track, has become a desired method of drug delivery for a number of reasons. This form of drug delivery by injection may enhance the effect of the substance being delivered and ensure that the unaltered medicine reaches its intended site at a significant concentration. Similarly, undesired side effects associated with other routes of delivery, such as systemic toxicity, can potentially be avoided through parenteral delivery. By bypassing the digestive system of a mammalian patient, one can avoid degradation of the active ingredients caused by the catalytic enzymes in the digestive tract and liver and ensure that a necessary amount of drug, at a desired concentration, reaches the targeted site.

Traditionally, manually operated syringes and injection pens have been employed for delivering parenteral drugs to a patient. More recently, parenteral delivery of liquid medicines into the body has been accomplished by administering bolus injections using a needle and reservoir, continuously by gravity driven dispensers, or via transdermal patch technologies. Bolus injections can imperfectly match the clinical needs of the patient, and may require larger individual doses than are desired at the specific time they are given. Continuous delivery of medicine through gravity-feed systems compromises the patient's mobility and lifestyle, and limits the therapy to simplistic flow rates and profiles. Another form of drug delivery, transdermal patches, similarly has its restrictions. Transdermal patches often require specific molecular drug structures for efficacy, and the control of the drug administration through a transdermal patch is severely limited.

Ambulatory infusion pumps have been developed for delivering liquid medicaments to a patient. These infusion devices have the ability to offer sophisticated fluid delivery profiles accomplishing bolus requirements, continuous infusion and variable rate delivery. These infusion capabilities usually result in better efficacy of the drug and therapy and less toxicity to the patient's system. Currently available ambulatory infusion devices are expensive, difficult to program and prepare for infusion, and tend to be bulky, heavy and very fragile. Filling these devices can be difficult and require the patient to carry both the intended medication as well as filling accessories. The devices often require specialized care, maintenance, and cleaning to assure proper functionality and safety for their intended long-term use, and are not cost-effective for patients and healthcare providers.

As compared to syringes and injection pens, pump type delivery devices can be significantly more convenient to a patient, in that doses of the drug may be calculated and delivered automatically to a patient at any time during the day or night. Furthermore, when used in conjunction with metabolic sensors or monitors, pumps may be automatically controlled to provide appropriate doses of a fluidic medium at appropriate times of need, based on sensed or monitored metabolic levels. As a result, pump type delivery devices have become an important aspect of modern medical treatments of various types of medical conditions, such as diabetes, and the like.

While pump type delivery systems have been utilized to solve a number of patient needs, manually operated syringes and injection pens often remain a preferred choice for drug delivery as they now provide integrated safety features and can easily be read to identify the status of drug delivery and the end of dose dispensing. However, manually operated syringes and injection pens are not universally applicable and are not preferred for delivery of all drugs. There remains a need for an adjustable (and/or programmable) infusion system that is precise and reliable and can offer clinicians and patients a small, low cost, light weight, simple to use alternative for parenteral delivery of liquid medicines.

There is a strong market demand for drug delivery devices which are easy-to-use, cost-efficient, and which include integrated safety features. However, manufacturing of such devices can be cost intensive, which results in higher costs to patients. Much of the manufacturing costs can be attributed to the need to maintain a sterile fluid pathway from the drug container to the needle, prior to introduction of the drug to the patient. Some commercial products seek to maintain the sterility of the device by manufacturing the components in a non-sterile environment and then sterilizing the entire device. A recognized downside of such processes is the need to separately fill the drug container after the device sterilization, but prior to drug injection, as most pharmaceutical compounds are not capable of withstanding the device sterilization process. Alternatively, the drug delivery device may be manufactured as a pre-filled device, wherein the device is filled with the drug aseptically during assembly. Such manufacturing processes may be costly since the entire process must be kept sterile and because the fill and assembly lines need to be specially-tailored for the device. Accordingly, this adds substantial operating costs to pharmaceutical companies and contract drug-fillers.

Drug delivery devices are generally prepared by molding or shaping the various components and then assembling the components. The assembling steps and other processing operations typically produce a device that subsequently must be cleaned to remove particulates adhering to the surfaces to satisfy cleanliness standards for drug delivery devices. After cleaning, conventional drug delivery devices are packaged and sterilized. Such delivery devices have been classified into several general types. The first type is assembled and placed in sterile packaging which can be shipped with a vial or ampoule of a drug or other injectable solution. The vial or ampoule is generally made of glass or other clear material that does not interfere with the stability of the drug during prolonged storage. The delivery device is filled with the drug or other solution at the point of use and injected into the patient. These devices have the disadvantage of increasing the time and difficulty of filling the device at the point of use with increased possibility of contamination of the delivery device and/or drug solution. There is a further risk of glass particles from the ampoules contaminating the drug solution when the ampoules are opened.

Several of these disadvantages are overcome by providing prefilled delivery devices which can be filled with a suitable drug solution prior to use. Prefilled delivery devices, as the term is known in the art, are devices that are filled by the drug manufacturer and shipped to the health care provider or self-administering patient in a condition that is ready for use. Prefilled delivery devices have the advantage of convenience and ease of application with reduced risk of contamination of the drug solution. Prefilled drug delivery devices are generally assembled and packaged in clean rooms to maintain proper cleanliness levels. The clean rooms are equipped with extensive filter assemblies and air control systems to remove particulates and pyrogens from the air in the room and to prevent particulates and pyrogens from entering the room. The operators and other personnel in the clean room are required to wear appropriate protective garments to reduce contamination of the air and the drug delivery devices being manufactured or assembled. As people and equipment enter and leave the clean room, the risk of contamination and introduction of foreign particulates and pyrogens increases. Various operations are able to form clean and sterile drug delivery devices. However, subsequent handling, filling and printing of the drug delivery device can contaminate the device. It is then necessary to clean and sterilize such conventional drug delivery devices before use. Accordingly, there is a continuing need in the industry for an improved system for manufacturing and assembling clean and sterile medical devices and filling such devices.

SUMMARY

The present invention provides container connections which are user-initiated and which maintain the sterility of the fluid pathway, and drug delivery pumps which incorporate such sterile fluid pathway connections to drug containers, the methods of operating such devices, and the methods of assembling such devices. The fluid pathway connections of the present invention provide integrated safety features which ensure the sterility of the fluid pathway before, during, and after drug delivery. In one aspect, the fluid pathway remains disconnected from the drug container until the connection and the device are initiated by the user. In a second aspect, the fluid pathway maintains the sterility of the piercing member prior to connection with the drug container within a sterile volume within a cavity of a pierceable seal to enable connection upon activation by the user. Upon activation by the user, the piercing member of the fluid pathway connection is caused to pierce the pierceable seal of the drug container to connect the fluid pathway and enable fluid flow through the fluid pathway for drug delivery into the body of the user. Accordingly, the novel devices of the present invention alleviate one or more of the problems associated with prior art devices, such as those referred to above.

In at least one embodiment, the fluid pathway connection assemblies include a piercing member and a sleeve. The piercing member may be constructed of a hollow cylinder, such as a hollow steel needle. The sleeve and piercing member are engaged such that they translate together as a unit. The sleeve may, in one embodiment, be constructed of a polymer material and may be formed through an overmolding process. The sleeve may alternatively be formed by any process known by one skilled in the art.

In an initial configuration, a portion of the piercing member is disposed within a cavity formed by the piercing member. Additionally, a portion of the sleeve is in a sealing engagement with the pierceable seal such that sterile volume is formed within the cavity of the pierceable seal. In the initial configuration, at least a portion of the piercing member is disposed within this sterile volume.

Upon activation, relative movement of the pierceable seal with respect to the piercing member causes the piercing member to pierce the pierceable seal and connect a fluid flowpath from the drug container, through the piercing member, a fluid conduit, and a needle insertion mechanism for delivery to a target location.

A first embodiment is a fluid pathway connection assembly. The assembly comprises a hollow needle piercing member, a sleeve fixedly engaged with the piercing member and a pierceable seal configured to sealingly engage the piercing member or the sleeve. In sealing engagement, the piercing member or the sleeve and the pierceable seal form a volume within which a portion of the piercing member is disposed. The fluid pathway connection assembly is activated by relative movement between the piercing member and the pierceable seal and activation causes the piercing member to pierce the pierceable seal, thereby establishing a fluid flowpath through the pierceable seal. Upon incorporation of the assembly into a sealed fluid flowpath, the volume is isolated from the environment and maintains the sterile condition of the portion of the piercing member disposed therein.

In an aspect of the first embodiment, the hollow needle piercing member is a rigid, hollow needle. In another aspect of the first embodiment, the hollow needle piercing member is bent. In another aspect of the first embodiment, the sleeve comprises a flange. In a further aspect of the first embodiment, the hollow needle piercing member is bent, the sleeve comprises a flange and at least a portion of the bent hollow needle piercing member is disposed within the flange. In another aspect of the first embodiment, the sleeve includes side channels to facilitate sterilization. In another aspect of the first embodiment, the pierceable seal is configured to sealingly engage the sleeve and, in sealing engagement, the sleeve and the pierceable seal form a volume within which a portion of the piercing member is disposed. In another aspect of the first embodiment, the pierceable seal includes one or more sealing ribs for sealingly engaging the piercing member or the sleeve. In another aspect of the first embodiment, the pierceable seal includes a recess and a tip of the piercing member is disposed within the recess upon establishment of the fluid flowpath through the pierceable seal. In another aspect of the first embodiment, the assembly further comprises a retainer that restricts deformation of the pierceable seal or prevents inadvertent relative movement between the piercing member and the pierceable seal. In another aspect of the first embodiment, one or more of the piercing member, the sleeve and the pierceable seal includes a vent which allows for evacuation of the volume. In another aspect of the first embodiment, the assembly further comprises a crimp cap for securing the pierceable seal to a drug container. In another aspect of the first embodiment, the pierceable seal is configured to sealingly engage a drug container.

It will be appreciated that the fluid connection assemblies described herein include a fluid connection assembly of the first embodiment, or any aspect or combination of aspects thereof.

A second embodiment is a drug delivery pump, comprising a fluid pathway connection assembly of the first embodiment, or any aspect or combination of aspects thereof.

A third embodiment is a drug delivery pump. The drug delivery pump comprises a pump housing including an activation mechanism, a power and control system, a drive mechanism including a drug container, an insertion mechanism for delivering drug fluid to a target, a fluid pathway connection assembly and a fluid conduit that fluidly connects the fluid pathway connection assembly to the insertion mechanism. The fluid pathway connection assembly comprises a hollow needle piercing member, a sleeve fixedly engaged with the piercing member and a pierceable seal configured to sealingly engage the piercing member or the sleeve and the drug container. In sealing engagement, the piercing member or the sleeve and the pierceable seal form a volume within which a portion of the piercing member is disposed. Actuation of the activation mechanism initiates the power and control system, which activates the fluid pathway connection assembly, thereby establishing a fluid flowpath from the drug container through the fluid pathway connection assembly and the fluid conduit to the insertion mechanism. Initiation of the power and control system also activates the drive mechanism, thereby driving drug fluid through the fluid flowpath. The fluid pathway connection assembly is activated by relative movement between the piercing member and the pierceable seal and activation causes the piercing member to pierce the pierceable seal, thereby establishing a fluid flowpath through the fluid pathway connection assembly. The volume is isolated from the environment and maintains the sterile condition of the portion of the piercing member disposed therein. In an aspect of the third embodiment, the drug delivery pump further comprises an on-body sensor. In another aspect of the third embodiment, the drug container contains drug fluid.

In another aspect of the third embodiment, the drug delivery pump comprises a fluid connection assembly of the first embodiment, or any aspect or combination of aspects thereof.

A fourth embodiment is a method of operating a drug delivery pump. The drug delivery pump comprises an activation mechanism, a power and control system, a drive mechanism including a drug container, an insertion mechanism for delivering drug fluid to a target, a fluid pathway connection assembly and a fluid conduit that fluidly connects the fluid pathway connection assembly to the insertion mechanism. The fluid pathway connection assembly includes a hollow needle piercing member, a sleeve fixedly engaged with the piercing member and a pierceable seal configured to sealingly engage the piercing member or the sleeve and the drug container, wherein, in sealing engagement, the piercing member or the sleeve and the pierceable seal form a volume within which a portion of the piercing member is disposed and which, upon incorporation of the assembly into a sealed fluid pathway, is isolated from the environment and maintains the sterile condition of the portion of the piercing member disposed therein. The method comprises activating the activation mechanism, actuating the insertion mechanism, actuating the fluid pathway connection assembly and initiating the power and control system to activate the drive mechanism to drive fluid drug through the drug delivery pump. Actuating the fluid pathway connection assembly causes the piercing member to pierce the pierceable seal, thereby establishing a fluid flowpath from the drug container through the fluid pathway connection assembly and the fluid conduit to the insertion mechanism. Fluid drug is thus delivered to the target.

It will be appreciated that the methods of operating a drug delivery pump described herein include a drug delivery pump comprising a fluid pathway connection assembly of the first embodiment, or any aspect or combination of aspects thereof, and/or a drug delivery pump of the second or third embodiment, or any aspect or combination of aspects thereof.

A fifth embodiment is a method of assembling a fluid pathway connection assembly and a drug container. The method comprises providing a fluid pathway connection assembly including a hollow needle piercing member, a sleeve and a pierceable seal configured to sealingly engage the piercing member or the sleeve, the pierceable seal having a cavity. The pierceable seal is inserted, at least partially, into an end of a drug container and securely constrained to the drug container. The piercing member is disposed, as least partially, in the cavity of the pierceable seal and the piercing member and the sleeve are fixedly secured to one another. The pierceable seal and the piercing member or the sleeve are sealingly engaged, thereby forming a volume. A portion of the piercing member is disposed within the volume. The volume, upon incorporation of the fluid pathway connection assembly into a sealed fluid flowpath, is isolated from the environment and maintains the sterile condition of the portion of the piercing member disposed therein. The fluid pathway connection assembly is activated by relative movement between the piercing member and the pierceable seal and activation causes the piercing member to pierce the pierceable seal. Thus, the fluid connection pathway and the drug container are assembled.

It will be appreciated that the methods of assembling a fluid pathway connection assembly and a drug container described herein include providing a fluid pathway connection assembly of the first embodiment, or any aspect or combination of aspects thereof.

BRIEF DESCRIPTION OF THE DRAWINGS

The foregoing will be apparent from the following more particular description of example embodiments, as illustrated in the accompanying drawings in which like reference characters refer to the same parts throughout the different views. The drawings are not necessarily to scale, emphasis instead being placed upon illustrating embodiments.

DETAILED DESCRIPTION

Figure 1A:
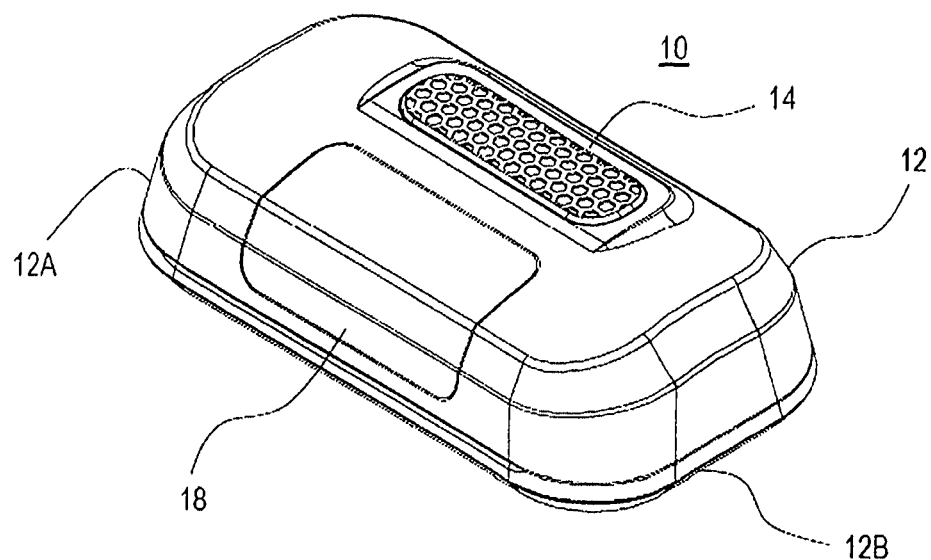
FIG. 1A is an isometric view of an embodiment of a drug delivery pump.

A description of example embodiments follows.

The teachings of all patents, published applications and references cited herein are incorporated by reference in their entirety.

As used herein to describe the drive mechanisms, drug delivery pumps, or any of the relative positions of the components of the present invention, the terms "axial" or "axially" refer generally to a longitudinal axis "A" around which the drive mechanisms are preferably positioned, although not necessarily symmetrically there-around. The term "radial" refers generally to a direction normal to axis A. The terms "proximal," "rear," "rearward," "back," or "backward" refer generally to an axial direction in the direction "P". The terms "distal," "front," "frontward," "depressed," or "forward" refer generally to an axial direction in the direction "D". As used herein, the term "glass" should be understood to include other similarly non-reactive materials suitable for use in a pharmaceutical grade application that would normally require glass, including but not limited to certain non-reactive polymers such as cyclic olefin copolymers (COC) and cyclic olefin polymers (COP). The term "plastic" may include both thermoplastic and thermosetting polymers. Thermoplastic polymers can be re-softened to their original condition by heat; thermosetting polymers cannot. As used herein, the term "plastic" refers primarily to moldable thermoplastic polymers such as, for example, polyethylene and polypropylene, or an acrylic resin, that also typically contain other ingredients such as curatives, fillers, reinforcing agents, colorants, and/or plasticizers, etc., and that can be formed or molded under heat and pressure. As used herein, the term "plastic" is not meant to include glass, non-reactive polymers, or elastomers that are approved for use in applications where they are in direct contact with therapeutic liquids that can interact with plastic or that can be degraded by substituents that could otherwise enter the liquid from plastic. The term "elastomer," "elastomeric" or "elastomeric material" refers primarily to cross-linked thermosetting rubbery polymers that are more easily deformable than plastics but that are approved for use with pharmaceutical grade fluids and are not readily susceptible to leaching or gas migration under ambient temperature and pressure. "Fluid" refers primarily to liquids, but can also include suspensions of solids dispersed in liquids, and gasses dissolved in or otherwise present together within liquids inside the fluid-containing portions of the pumps. According to various aspects and embodiments described herein, reference is made to a "biasing member", which may be any member that is capable of storing and releasing energy. Non-limiting examples include a spring, such as for example a coiled spring, a compression or extension spring, a torsional spring, and a leaf spring, a resiliently compressible or elastic band, or any other member with similar functions. In at least one embodiment of the present invention, the biasing member is a spring.

The novel devices of the present invention provide container connections which maintain the sterility and/or aseptic condition of the fluid pathway, and drug delivery pumps which incorporate such sterile fluid pathway connection assemblies to drug containers. Such devices are safe and easy to use, and are aesthetically and ergonomically appealing for self-administering patients. The fluid pathway connection may be initiated directly by the user, or may be activated by another mechanism of the device (as described herein) after some initial user step. The devices described herein incorporate features which make activation, operation, and lock-out of the device simple for even untrained users. The novel devices of the present invention provide these desirable features without problems associated with known prior art devices. Certain non-limiting embodiments of the novel drug delivery pumps, fluid pathway connection assemblies, and their respective components are described further herein with reference to the accompanying figures.

Conventional drug delivery devices often require filling at time-of-use because the terminal sterilization of the device cannot be completed with the pharmaceutical drug within the drug container. Various pharmaceutical drugs cannot withstand the temperatures, pressures, and other conditions necessary for sterilization of the device after assembly. In other words, because existing manufacturing processes require sterilization of the entire device, the drug cannot be "pre-filled" into the device prior to sterilization. This adds a complex step after final assembly of the device, which often requires costly additional equipment, handling of separate drug containers, and/or training of the patient to perform the filling step themselves prior to injection. Instead, the embodiments of the present invention enable the manufacture, assembly, and use of pre-filled drug delivery devices which maintain the sterility and/or aseptic condition of the fluid pathway assembly through the various manufacturing steps.

Additionally, because the drug delivery devices which incorporate the novel embodiments of the present invention do not need to be terminally sterilized, the components of the devices may be constructed of other, often less expensive, materials which would not normally withstand the sterilization environment. For example, less expensive plastics may be utilized for certain device components because they do not need to be sterilized after assembly. Furthermore, the embodiments of the present invention permit device architecture and/or component integration in ways which are not suitable for devices that require terminal sterilization. For example, when sterilization of the entire device is necessary, the device architecture often requires adequate spacing of components to permit the sterilization gas or material to effectively reach the target surfaces. Removing the need for terminal sterilization permits reduction or elimination of those spaces and allows for device architectures that offer smaller overall dimensions, human factors benefits, and/or industrial design options that are not available for devices that require terminal sterilization.

In other words, the embodiments of the present invention may allow the manufacturer to sterilize only the components which will be in contact with the drug fluid and/or which are necessary to maintain sterile and/or aseptic fluid pathways. These embodiments may also allow the pharmaceutical filler to maintain the sterility and/or aseptic condition of these components during the filling and finishing steps associated with the assembly of the drug delivery devices. Similarly, drug delivery devices which incorporate the fluid pathway connection assemblies of the present invention may have smaller or more efficient geometries as the device does not have to be configured for sterilization after assembly.

Additionally, the embodiments of the present invention allow for the utilization of standard fill-finish processes to fill the drug container. This greatly simplifies the manufacturing processes used to build drug delivery devices. Standard fill-finish processes utilize trays which hold multiple drug containers, such as syringes. The embodiments of the present invention enable a drug delivery device manufacturer, pharmaceutical company, or contract drug filler to fill the drug containers for infusion or injection pumps using the same standard fill-finish processes. These drug containers can be filled aseptically, as is common industry practice, in a cost-efficient manner. The drug container and the fluid pathway connection assembly can then be mated into a drug delivery device without requiring the remainder of the device components to be sterilized. Accordingly, embodiments of the present invention may provide novel components which enable the fluid pathway assemblies to be sterilized, assembled, filled, and incorporated into drug delivery devices in a cost-efficient and streamlined process.

In the processes of filling drug containers and other drug delivery devices, it is sometimes necessary to connect two or more sterile components or subassemblies. For example, wearable injectors or drug pumps may include a drug container which may be filled with a fluid drug using standard pharmaceutical fill-finish processes. After filling of the drug container, it may be necessary to connect the drug container to one or more additional components or subassemblies such that a fluid communication may be established between the drug container and these components. Maintaining the fluid path in an aseptic condition is critical, preventing the introduction of harmful microbes or particulates to the drug and/or fluid pathway.

The novel devices of the present invention provide fluid pathway connection assemblies with integrated safety features and drug delivery pumps which incorporate such fluid pathway connection assemblies. Such devices are safe and easy to use, and are aesthetically and ergonomically appealing for self-administering patients. The devices described herein incorporate features which make activation, operation, and lock-out of the device simple for even untrained users. The novel devices of the present invention provide these desirable features without any of the problems associated with known prior art devices. Certain non-limiting embodiments of the novel drug delivery pump, fluid pathway connection assemblies, and their respective components are described further herein with reference to the accompanying figures. The devices described herein may be configured for delivery of controlled substances and may further include features that prevent so-called "run-away" delivery of medicament. When delivering controlled substances, this may be an important safety feature to protect the patient. For example, some medicaments, such as insulin, can be dangerous, and potentially even deadly, when administered in too large a quantity and/or at too rapid of a rate. By providing such automatic safety stop mechanisms, the safety of the patient may be ensured.

Figure 1B:
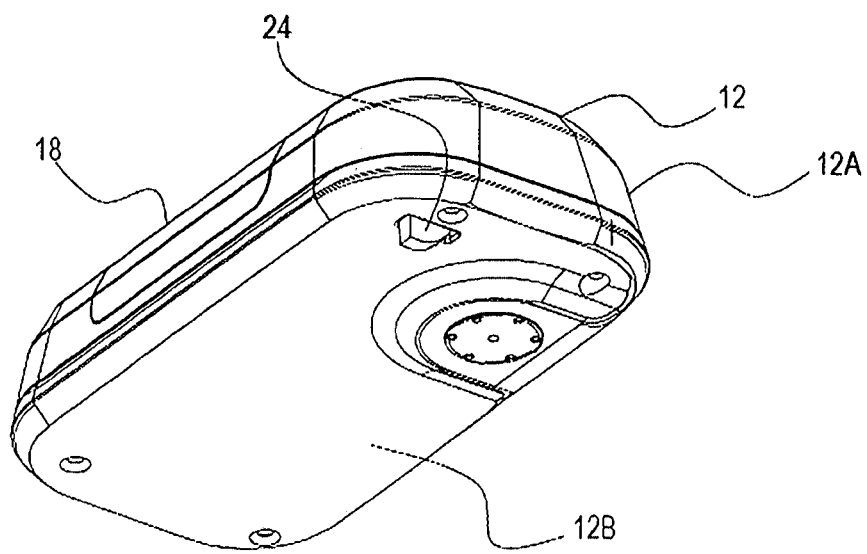
FIG. 1B shows an isometric view of the bottom of the drug delivery pump shown in FIG. 1A.
Figure 2A:
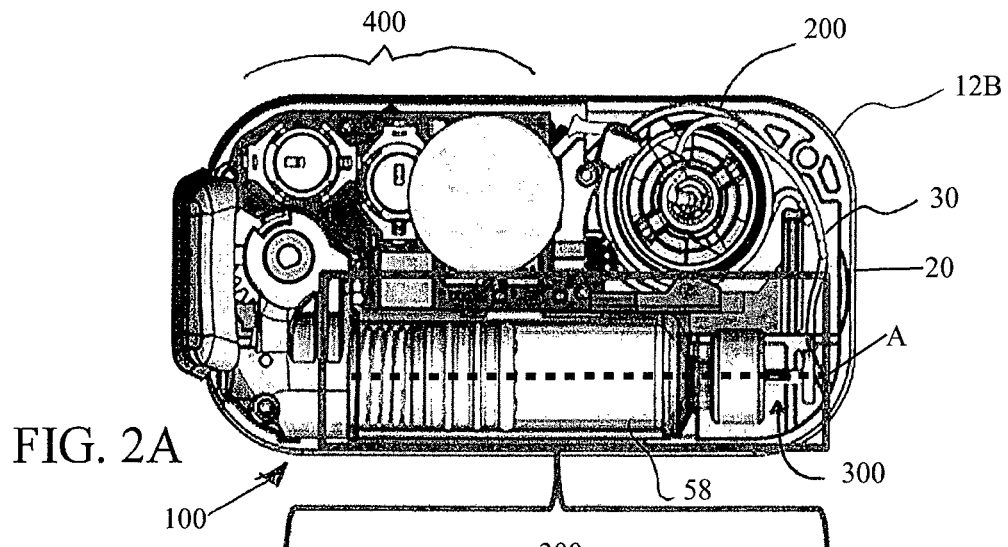
FIG. 2A shows a top view of an embodiment of a drug delivery pump of the present invention with a portion of the housing removed.
Figures 2B, 2C:
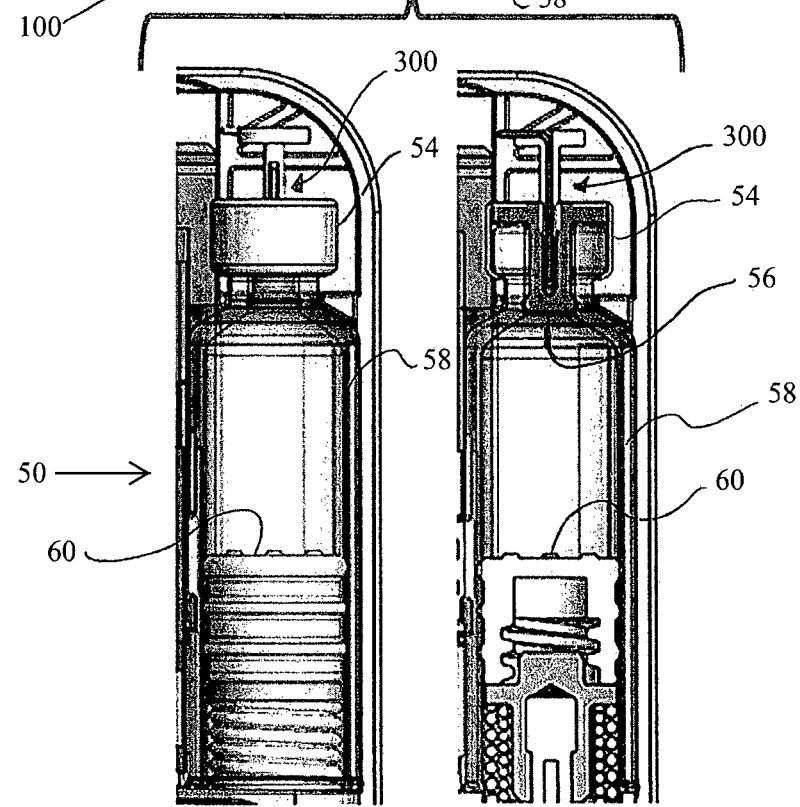
FIG. 2B shows a detailed top view of the embodiment of FIG. 2A.
FIG. 2C shows a detailed top cross-sectional view of the embodiment of FIG. 2A.

As used herein, the term "pump" is intended to include any number of drug delivery systems which are capable of dispensing a fluid to a target upon activation. Such drug delivery systems include, for example, injection systems, infusion pumps, bolus injectors, and the like. FIGS. 1A-1B show an exemplary drug delivery device according to at least one embodiment of the present invention. The drug delivery device may be utilized to administer delivery of a drug treatment into a target. As shown in FIGS. 1A-1B, the drug pump 10 includes a pump housing 12. Pump housing 12 may include one or more housing subcomponents which are fixedly engageable to facilitate easier manufacturing, assembly, and operation of the drug pump. For example, drug pump 10 includes a pump housing 12 which includes an upper housing 12A and a lower housing 12B. The drug pump may further include an activation mechanism 14, a status indicator (not shown), and a window 18. Window 18 may be any translucent or transmissive surface through which the operation of the drug pump may be viewed. As shown in FIG. 2, drug pump 10 further includes assembly platform 20, drive mechanism 100 having drug container 50, insertion mechanism 200, fluid pathway connection assembly 300, and power and control system 400. A sterile fluid conduit 30 may fluidly connect the fluid pathway connection assembly 300 with the insertion mechanism 200. One or more of the components of such drug pumps may be modular in that they may be, for example, pre-assembled as separate components and configured into position onto the assembly platform 20 of the drug pump 10 during manufacturing.

The pump housing 12 contains all of the device components and provides a means of removably attaching the device 10 to a target, such as tissue of a user. The pump housing 12 also provides protection to the interior components of the device 10 against environmental influences. The pump housing 12 is ergonomically and aesthetically designed in size, shape, and related features to facilitate easy packaging, storage, handling, and use by users who may be untrained and/or physically impaired. Furthermore, the external surface of the pump housing 12 may be utilized to provide product labeling, safety instructions, and the like. Additionally, as described above, housing 12 may include certain components, such as a status indicator (not shown) and window 18, which may provide operation feedback to the user.

In at least one embodiment, the drug pump 10 provides an activation mechanism 14 that is displaced by the user to trigger the start command to the power and control system 400. In a preferred embodiment, the activation mechanism is a start button 14 that is located through the pump housing 12, such as through an aperture in the upper housing 12A (as in FIG. 1A), or between upper housing 12A and lower housing 12B (not shown), and which contacts a control arm (not shown) of the power and control system 400. In at least one embodiment, the start button 14 may be a push button, and in other embodiments, may be an on/off switch, a toggle, or any similar activation feature known in the art. The pump housing 12 may also include a status indicator (not shown) and a window 18. In other embodiments, one or more of the activation mechanism 14, the status indicator, the window 18, and combinations thereof may be provided on the upper housing 12A or the lower housing 12B such as, for example, on a side visible to the user when the drug pump 10 is placed on the target. Housing 12 is described in further detail hereinafter with reference to other components and embodiments of the present invention.

Drug pump 10 is configured such that, upon activation by a user by actuation of the activation mechanism, the drug pump is initiated to: insert a fluid pathway into the target; enable, connect, or open necessary connections between a drug container, a fluid pathway, and a sterile fluid conduit; and force drug fluid stored in the drug container through the fluid pathway and sterile fluid conduit for delivery into a target. Each of these operations may begin simultaneously upon depression of the activation mechanism or, alternatively, one or more operations may be delayed. The fluid pathway connection may be initiated directly by the user, or may be activated by another mechanism of the device (as described herein) after some initial user step.

One or more optional safety mechanisms may be utilized, for example, to prevent premature activation of the drug pump. For example, an optional on-body sensor 24 may be provided in one embodiment as a safety feature to ensure that the power and control system 400, or the activation mechanism 14, cannot be engaged unless the drug pump 10 is in contact with the target. In one such embodiment, the on-body sensor is located on the bottom of lower housing 12B where it may come in contact with the target. Upon displacement of the on-body sensor, actuation of the activation mechanism is permitted. Accordingly, in at least one embodiment the on-body sensor 24 is a mechanical safety mechanism, such as for example a mechanical lock out, that prevents triggering of the drug pump 10 by the activation mechanism 14. In another embodiment, the on-body sensor may be an electro-mechanical sensor such as a mechanical lock out that sends a signal to the power and control system 400 to permit activation. In still other embodiments, the on-body sensor can be electrically based such as, for example, a capacitive- or impedance-based sensor which must detect tissue before permitting activation of the power and control system 400.

In at least one embodiment, housing 12 is configured to at least partially prevent harmful matter from entering the drug pump. For example, the housing may be configured to restrict the passage of fluids into the drug pump. This may allow the device to be worn in the shower, while swimming, or during other activities. Use of an electrically based skin sensor may eliminate potential points of entry into the drug pump. These concepts are not mutually exclusive and one or more combinations may be utilized within the breadth of the present invention to prevent, for example, premature activation of the drug pump. In a preferred embodiment, the drug pump 10 utilizes one or more mechanical on-body sensors. Additional integrated safety mechanisms are described herein with reference to other components of the novel drug pumps.

Power and Control System:

The power and control system 400 includes a power source, which provides the energy for various electrical components within the drug pump, one or more feedback mechanisms, a microcontroller, a circuit board, one or more conductive pads, and one or more interconnects. Other components commonly used in such electrical systems may also be included, as would be appreciated by one having ordinary skill in the art. The one or more feedback mechanisms may include, for example, audible alarms such as piezo alarms and/or light indicators such as light emitting diodes (LEDs). The microcontroller may be, for example, a microprocessor. The power and control system 400 controls several device interactions with the user and interfaces with the drive mechanism 100. In one embodiment, the power and control system 400 interfaces with the control arm to identify when the on-body sensor 24 and/or the activation mechanism 14 have been activated. The power and control system 400 may also interface with the status indicator of the pump housing 12, which may be a transmissive or translucent material which permits light transfer, to provide visual feedback to the user. The power and control system 400 interfaces with the drive mechanism 100 through one or more interconnects to relay status indication, such as activation, drug delivery, and end-of-dose, to the user. Such status indication may be presented to the user via auditory tones, such as through the audible alarms, and/or via visual indicators, such as through the LEDs. In a preferred embodiment, the control interfaces between the power and control system and the other components of the drug pump are not engaged or connected until activation by the user. This is a desirable safety feature that prevents accidental operation of the drug pump and may additionally maintain the energy contained in the power source during storage, transportation, and the like.

The power and control system 400 may be configured to provide a number of different status indicators to the user. For example, the power and control system 400 may be configured such that after the on-body sensor and/or trigger mechanism have been pressed, the power and control system 400 provides a ready-to-start status signal via the status indicator if device start-up checks provide no errors. After providing the ready-to-start status signal and, in an embodiment with the optional on-body sensor, if the on-body sensor remains in contact with the target, the power and control system 400 will power the drive mechanism 100 to begin delivery of the drug treatment through the fluid pathway connection assembly 300 and sterile fluid conduit. In a preferred embodiment of the present invention, the insertion mechanism 200 and the fluid pathway connection assembly 300 may be caused to activate directly or indirectly by user operation of the activation mechanism 14. During the drug delivery process, the power and control system 400 is configured to provide a dispensing status signal via the status indicator. After the drug has been administered into the target and after the end of any additional dwell time, to ensure that substantially the entire dose has been delivered to the target, the power and control system 400 may provide an okay-to-remove status signal via the status indicator. This may be independently verified by the user by viewing the drive mechanism and drug dose delivery through the window 18 of the pump housing 12. Additionally, the power and control system 400 may be configured to provide one or more alert signals via the status indicator, such as for example alerts indicative of fault or operation failure situations.

Other power and control system configurations may be utilized with the novel drug pumps of the present invention. For example, certain activation delays may be utilized during drug delivery. As mentioned above, one such delay optionally included within the system configuration is a dwell time which ensures that substantially the entire drug dose has been delivered before signaling completion to the user. Similarly, activation of the device may require a delayed depression (i.e., pushing) of the activation mechanism 14 of the drug pump 10 prior to drug pump activation. Additionally, the system may include a feature which permits the user to respond to the end-of-dose signals and to deactivate or power-down the drug pump. Such a feature may similarly require a delayed depression of the activation mechanism, to prevent accidental deactivation of the device. Such features provide desirable safety integration and ease-of-use parameters to the drug pumps. An additional safety feature may be integrated into the activation mechanism to prevent partial depression and, therefore, partial activation of the drug pumps. For example, the activation mechanism and/or power and control system may be configured such that the device is either completely off or completely on, to prevent partial activation. Such features are described in further detail hereinafter with regard to other aspects of the novel drug pumps.

Insertion Mechanism:

A number of insertion mechanisms may be utilized within the drug pumps of the present invention. In at least one embodiment, the insertion mechanism 200 includes an insertion mechanism housing having one or more lockout windows, and a base for connection to the assembly platform and/or pump housing (as shown in FIG. 1B and FIG. 2A). The connection of the base to the assembly platform 20 may be, for example, such that the bottom of the base is permitted to pass-through a hole in the assembly platform to permit direct contact of the base to the target, as shown in FIG. 1B.

In such configurations, the bottom of the base may include a sealing membrane that is removable prior to use of the drug pump 10. The insertion mechanism may further include one or more insertion biasing members, a needle, a retraction biasing member, a cannula, and a manifold. The manifold may connect to sterile fluid conduit to permit fluid flow through the manifold, cannula, and into the target during drug delivery.

As used herein, "needle" is intended to refer to a variety of needles including but not limited to conventional hollow needles, such as a rigid hollow steel needles, and solid core needles more commonly referred to as a "trocars." In some embodiments, the needle is a 27 gauge solid core trocar and in other embodiments, the needle may be any size needle suitable to insert the cannula for the type of drug and drug administration (e.g., subcutaneous, intramuscular, intradermal, etc.) intended. In one embodiment, the insertion mechanism may generally be as described in International Patent Application No. PCT/US2012/53174, published as WO 2013/033421 A2, International Patent Application No. PCT/US2012/053241, published as WO 2013/033467 A2, or International Patent Application Nos. PCT/US2015/052815 and PCT/US2016/017534, which are incorporated by reference herein in their entirety for all purposes.

Drive Mechanism:

A number of drive mechanisms may be utilized to force fluid from a drug container 50 for delivery into the target. In one such embodiment, the drive mechanism 100 includes a drive housing, a status switch interconnect, and a drug container 50 having a crimp cap 54, a pierceable seal 56, a barrel 58, and a plunger seal 60 within the barrel. The drug container may contain a drug fluid, within the barrel between the pierceable seal and the plunger seal, for delivery through the insertion mechanism and drug pump into the target. The seals described herein may be comprised of a number of materials but are, in a preferred embodiment, comprised of one or more elastomers or rubbers. The drive mechanism may further include a connection mount to guide the insertion of the piercing member of the fluid pathway connection assembly into the barrel 58 of the drug container. The drive mechanism 100 may further contain one or more drive biasing members, one or more release mechanisms, and one or more guides. The components of the drive mechanism function to force a fluid from the drug container out through the pierceable seal, or preferably through the piercing member of the fluid pathway connection assembly, for delivery through the fluid pathway connection assembly, sterile fluid conduit, and insertion mechanism into the target.

In one particular embodiment, the drive mechanism 100 employs one or more compression springs as the biasing member(s). Upon activation of the drug pump by the user, the power and control system 400 may be actuated to directly or indirectly release the compression spring(s) from an energized state. Upon release, the compression spring(s) may bear against and act upon the plunger seal to force the fluid drug out of the drug container. The fluid pathway connection assembly 300 may be connected through the pierceable seal prior to, concurrently with, or after activation of the drive mechanism to permit fluid flow from the drug container, through the fluid pathway connection assembly, sterile fluid conduit, and insertion mechanism, and into the target for drug delivery. In at least one embodiment, the fluid flows through only a manifold or a needle, and a cannula, of the insertion mechanism, thereby maintaining the sterility of the fluid pathway before and during drug delivery. Such components and their functions are described in further detail hereinafter.

The components of the drive mechanism 100, upon activation, may be used to drive axial translation in the distal direction of the plunger seal of the drug container. Optionally, the drive mechanism 100 may include one or more compliance features which enable additional axial translation of the plunger seal to, for example, ensure that substantially the entire drug dose has been delivered to the target and make sure that the feedback contact mechanisms have connected. Additionally or alternatively, the plunger seal, itself, may have some compressibility permitting a compliance push of drug fluid from the drug container. The drive mechanism 100 may similarly include one or more status indication mechanisms, such as interconnects and contacts, to measure and communicate the status of the drive mechanism before, during, and after operation of the drive mechanism and the device to the user. Furthermore, the drive mechanism 100 may include one or more safety mechanisms, such as premature activation prevention mechanisms, to enhance the safety and usability of the mechanism and the device. Further details related to the drive mechanism 100 are provided herein with reference to other components of the drug pump. The insertion mechanism may generally be as described in International Patent Application No. PCT/US2012/05174, published as WO 2013/033421 A2, International Patent Application No. PCT/US2013/057259, published as WO 2014-036239 A2, or International Patent Application No. PCT/US2016/021585, which are incorporated by reference herein in their entirety for all purposes.

Figure 5:
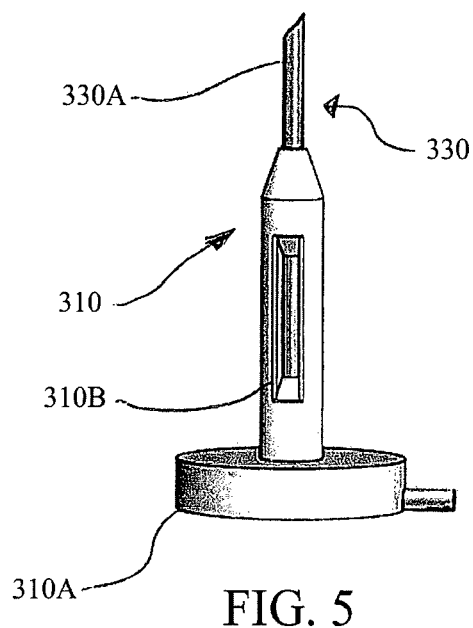
FIG. 5 shows an isometric view of an embodiment of a fluid pathway connection assembly.

Fluid Pathway Connection Assembly:

In at least one embodiment, the fluid pathway connection assembly includes a piercing member 330 and a sleeve 310, as shown in FIG. 5. In one embodiment, the piercing member 330 is a rigid, hollow needle. The piercing member may be a hollow steel needle, such as a 27 gauge needle. A sleeve 310 may be fixedly engaged with the piercing member 330. The sleeve 310 may be formed by an overmolding process or, alternatively, may be a component that is affixed to the piercing member 330 using adhesive. Alternatively, or additionally, the sleeve 310 may be configured to form a mechanical lock to prevent relative movement between the sleeve 310 and piercing member 330. The piercing member 330 may also be bent. A bent needle allows the fluid pathway connector to be compact in size while allowing for the connection of the piercing member 330 to the fluid conduit 30. In some embodiments, such as when the sleeve 310 is formed using an overmolding procedure, the piercing member 330 may be bent after the sleeve 310 is assembled to the piercing member 330.

Figures 3A, 3B:
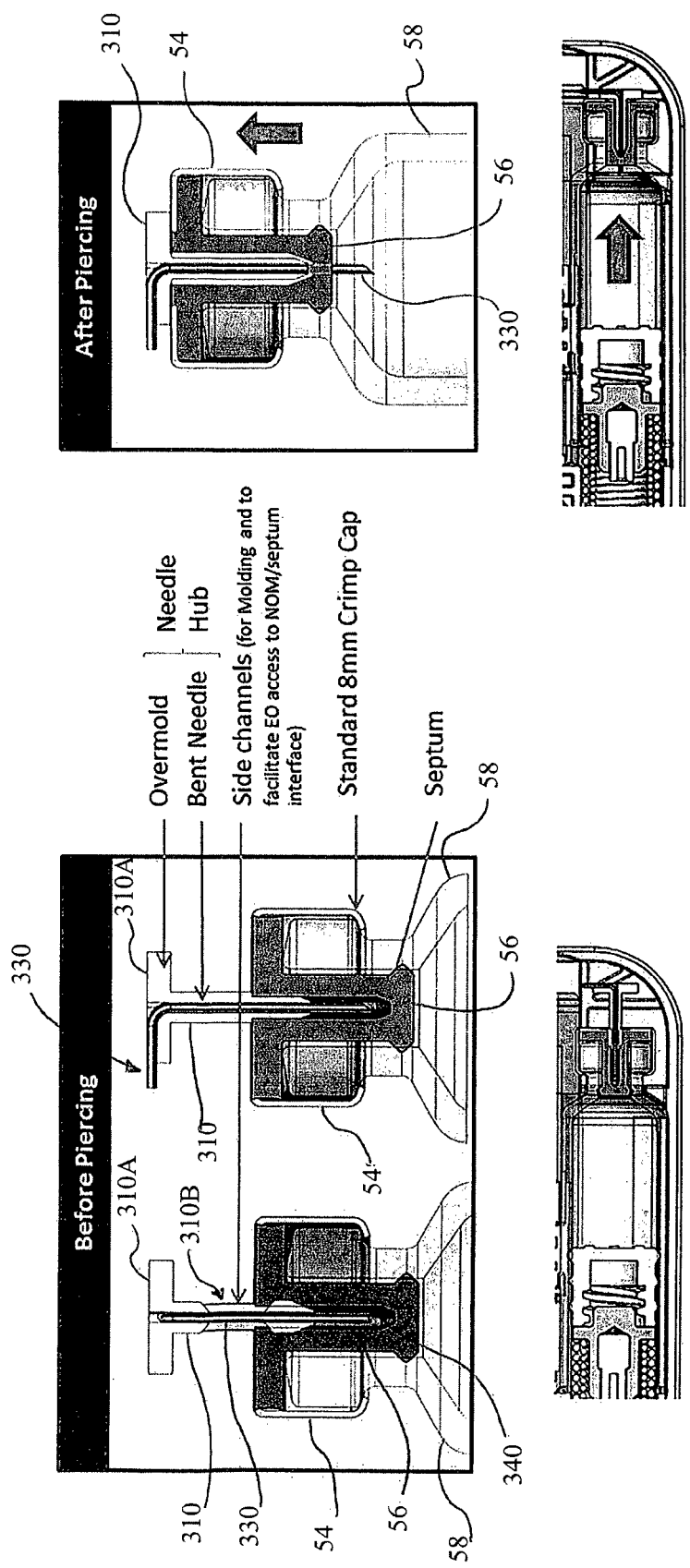
FIG. 3A shows a detailed cross-sectional view of a drug container and fluid pathway connection assembly in an initial configuration.
FIG. 3B shows a detailed cross-sectional view of the drug container and fluid pathway connection assembly of FIG. 3A in a connected configuration.
Figure 4:
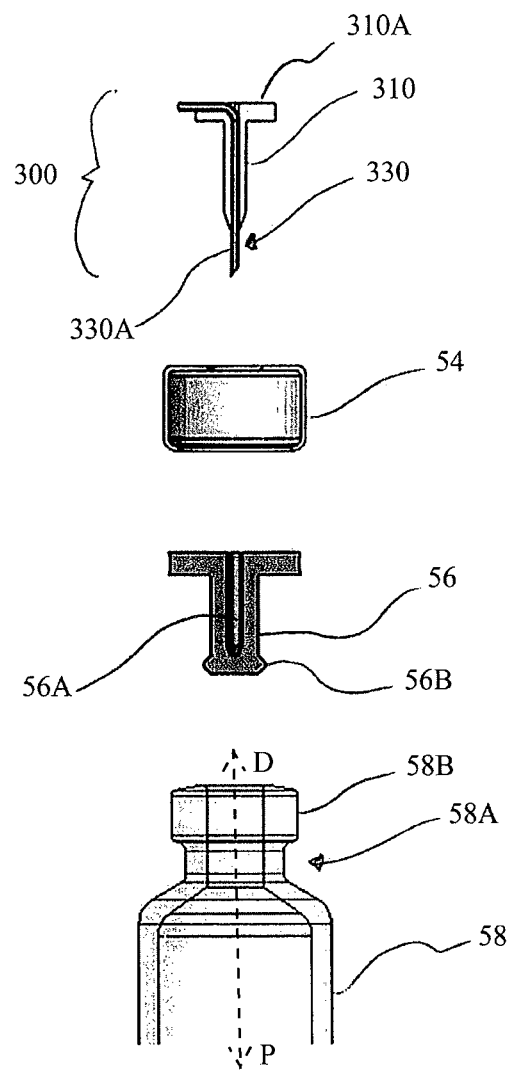
FIG. 4 shows an exploded view of a drug container and fluid pathway connection assembly.

As shown in FIG. 3A, a pierceable seal 56 may be, at least partially, disposed within the distal end of the drug container 50. The pierceable seal 56 may be constructed of any material but is preferably constructed from an elastomeric material. The pierceable seal 56 may include one or more circumferential ribs 56B configured to sealingly engage an internal face of the drug container. The pierceable seal 56 may be held in position within the drug container by crimp cap 54. For example, the crimp cap may be an aluminum cap which is crimped over the neck 58A and/or collar 58B of the drug container 58, at its distal end, and over the face of the pierceable seal 56, at its proximal end.

The pierceable seal may be configured to form a cavity 56A within which a portion of piercing member 330 may be disposed. As shown in FIG. 3, in an initial configuration, the proximal portion 330A of the piercing member 330 is disposed within the cavity 56A formed by the pierceable seal 56. In this configuration, the sleeve 310 is in sealing engagement with the pierceable seal 56. As a result, a sterile volume 340 is formed between the sleeve 310 and the proximal face of the cavity 56A. Hence, the proximal portion 330A of the piercing member is isolated from the environment. The fluid pathway connection 300 may remain in this configuration during storage and shipping of the device and until activation of delivery, by the user. The proximal tip of the piercing member 330 may be partially inserted into the pierceable seal 56 in this storage configuration. Alternatively, the distal tip of the piercing member 330 may be positioned within sterile volume 340. In such a configuration, the tip of the piercing member 330 may be sterilized in the assembled configuration. This may allow the use of an ethylene oxide sterilization process.

Figure 6:
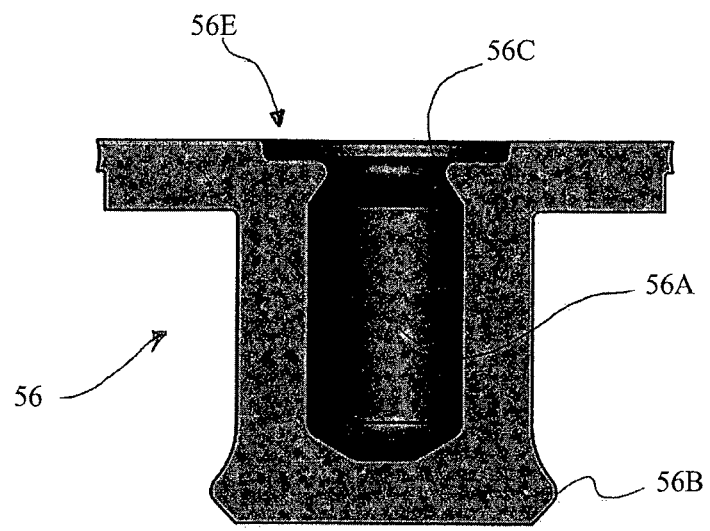
FIG. 6 shows a cross-sectional view of a pierceable seal according to at least one embodiment of the present invention.

In at least one embodiment, as shown in FIG. 6, cavity 56A of pierceable seal 56 includes a sealing rib 56C configured for engagement with piercing member 330 or sleeve 310. Contact between sealing rib 56C and sleeve 310 or piercing member 330 ensures that the sterility and/or aseptic condition of the interior of the cavity is maintained throughout the operation of the device. Although a single sealing rib is shown, more than one sealing rib may be utilized. In addition, the one or more sealing ribs may be positioned at any position along cavity 56A. In a preferred embodiment, as shown in FIG. 6, at least one sealing rib is positioned near to the distal end of cavity 56A.

Figure 7:
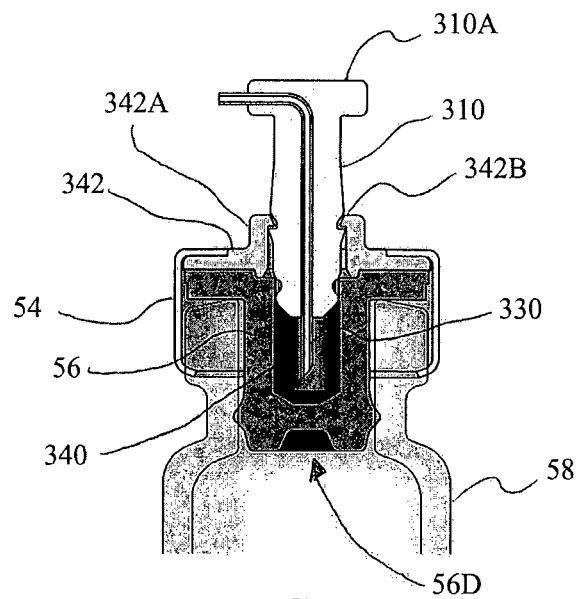
FIG. 7 shows a side cross-sectional view of a drug container and fluid pathway connection assembly according to at least one embodiment of the present invention.

As shown in FIG. 7, in at least one embodiment, pierceable seal 56 may include additional features such as proximal recess 56D which is configured to reduce the amount of "dead-space" in the system. In such a configuration, after opening of the fluid pathway connection, the proximal tip of the piercing member 330 may be disposed within the proximal recess 56D. This allows nearly all of the contents of the drug container to be expelled during operation. The pierceable seal 56 may further include features which assist in preventing the collapse of cavity 56A. These features may include a bore 56E within which retainer 342 is partially disposed. The position of retainer 342 within the bore 56E may restrict deformation of the pierceable seal 56 during assembly of the piercing member 330 to the pierceable seal 56.

Upon activation, relative movement between the drug container 58 and piercing member 330 causes the fluid pathway connection 300 to transform to a second configuration wherein the piercing member 330 has pierced the pierceable seal 56. This piercing causes a fluid flowpath to be established from the drug container 58, through the piercing member 330, fluid conduit 30, and needle insertion mechanism 200 for delivery to the target. The relative movement may, for example, result from translation of the sleeve 310 and piercing member 330 in the proximal direction. This may be caused by actuation of the actuation mechanism. In one embodiment, the sleeve 310 and piercing member 330 are biased for proximal translation for example by a biasing member, such as a spring. Prior to activation, a component of the drug delivery pump may prevent proximal translation of the sleeve 310 and piercing member 330. Upon actuation of the activation mechanism, the translation prevention feature may be transformed such that it no longer restricts translation of the fluid pathway connection. As a result, decompression or de-energizing of the biasing member causes the sleeve and piercing member to translate proximally and pierce the pierceable seal 56.

Alternatively, the relative movement may result from translation of the drug container 58 in the distal direction. Translation of the drug container 58 may be caused by activation of the drive mechanism 100. Because the fluid flowpath is initially not open, and the drug container's enclosed volume is fixed, the resulting translation of the plunger seal 60 within the drug container 58 may be transferred to the drug container 58 through hydraulic and/or pneumatic pressure within the drug container 58. Movement of the piercing member 330 may be restricted by, for example, engagement of the sleeve 310 with a portion of the housing 12. Hence, translation of the drug container 58 causes the piercing member 330 to pierce the pierceable seal 56 to open a fluid flowpath through the piercing member 330.

In another embodiment, at least a portion of the pierceable seal 56 translates, in the distal direction, with respect to both the drug container 58 and the pierceable seal 56. This translation may be in response to hydraulic and/or pneumatic pressure within the drug container. For example, a portion of the pierceable seal may deform as described in U.S. Patent Application Publication No. US2015/0057613, which is incorporated herein by reference in its entirety. This translation of a portion of the pierceable seal 56 causes the piercing member 330 to pierce the pierceable seal 56 and establish a fluid flowpath as described above.

The sleeve 310 may include side channels 310B, as shown in FIG. 5, to facilitate the use of ethylene oxide sterilization. The sleeve 310 may also include a flange 310A within which at least a portion of the second leg of the bent needle is disposed. This may facilitate the alignment of the fluid pathway connection 300 during assembly. The flange 310A may also be used to control the position of the fluid pathway connection assembly 300 relative to the housing 12 and/or drug container 58.

Additionally, as shown in FIG. 7, one or more components may include features that resist inadvertent proximal movement of the piercing member 330 with respect to the pierceable seal 56. Additionally, these features may prevent distal movement of the piercing member 330 with respect to pierceable seal 56 (i.e., pull-out of the piercing member 330). For example, the sleeve 310 may include one or more radially outward extending features such as a barb or ring which engages the pierceable seal 56 and prevents proximal movement of the sleeve 310 and piercing member 56. Optionally, the pierceable seal 56 may include one or more corresponding radial recesses configured to engage the radially extending features of the sleeve 310. Alternatively, or additionally, the pierceable seal 56 may include one or more radially inward extending features which engage the sleeve 310. The radially inwardly extending features may be integrally formed in pierceable seal or, alternatively, these features may be a portion of a separate component, such as retainer 342, shown in FIG. 7. Retainer 342 may be secured in position by cap 54. Retainer 342 may include one or more extensions 342A with teeth 342B configured to engage sleeve 310. This engagement would prevent inadvertent relative motion of the drug container and piercing member. Sufficient force applied to either the drug container or sleeve would cause the extensions 342A to flex radially outward, allowing relative translation of the drug container toward the piercing member or relative translation of the piercing member toward the drug container. The extensions 342A may be oriented such that they extend away from the drug container as shown in FIG. 7 or, alternatively, they may be positioned at least partially within the drug container and/or pierceable seal.

One or more of the pierceable seal 56, sleeve 310, and piercing member 330 may include a vent which allows for the evacuation of the volume enclosed by the sterile volume 340. The vent may allow air to escape from the sterile volume 340 while preventing contaminants from entering this volume. For example, the vent may be enclosed by a filter, which prevents particulates and other contaminants from entering the sterile volume 340.

Fluid pathways of the present disclosure provide several advantages. Such assemblies are simple and cost-efficient. Additionally, they allow the drug container, pierceable seal, and crimp cap to be assembled independently of the fluid pathway connection. This allows for simplified assembly using traditional equipment and processes. Additionally, the drug container, fluid pathway connection assembly, and needle insertion mechanism may be assembled together prior to sterilization and drug filling. These components form a closed fluid flowpath, avoiding the need to sterilize other components of the drug delivery device.

The fluid pathway connections of the present invention may include one or more lockout features which prevent inadvertent activation. For example, translation of the sleeve and/or piercing member may be prevented if the on-body sensor is not in an activated state (i.e., in contact with the target site). The on-body sensor may form, or be in communication with, an interlock which is, initially, in contact with the flange 310A, or other aspect of, the sleeve 310. Activation of the on-body sensor, by placement of the device against the target site, causes a transformation of the interlock such that it allows translation of the fluid pathway connector.

It will be appreciated from the above description that the fluid pathway connection assemblies and drug pumps disclosed herein provide an efficient and easily-operated system for automated drug delivery from a drug container. The novel devices of the present disclosure provide container connections that maintain the aseptic condition of the fluid pathway, and drug delivery pumps which incorporate such fluid pathway connection assemblies to drug containers. Such devices are safe and easy to use, and are aesthetically and ergonomically appealing for self-administering patients. The devices described herein incorporate features which make activation, operation, and lock-out of the device simple for even untrained users. Because the fluid path is disconnected until drug delivery is desired by the user, the aseptic condition of the fluid pathway connection assembly, the drug container, the drug fluid, and the device as a whole is maintained. These aspects provide highly desirable storage, transportation, and safety advantages to the user. In at least one embodiment, the power and control system, the assembly platform, the activation mechanism, the housing, and other components of the drug pump do not need to be sterilized. This greatly improves the manufacturability of the device and reduces associated assembly costs. Accordingly, the devices of the present invention do not require terminal sterilization upon completion of assembly. A further benefit is that the components described herein are designed to be modular such that, for example, housing and other components of the pump drug may readily be configured to accept and operate the fluid pathway connections described herein.

Assembly and/or manufacturing of fluid pathway connection assembly 300, drug delivery pump 10, or any of the individual components may utilize a number of known materials and methodologies in the art. For example, a number of known cleaning fluids such as isopropyl alcohol and hexane may be used to clean the components and/or the devices. A number of known adhesives or glues may similarly be employed in the manufacturing process. Additionally, known siliconization and/or lubrication fluids and processes may be employed during the manufacture of the novel components and devices. Furthermore, known sterilization processes may be employed at one or more of the manufacturing or assembly stages to ensure the sterility of the final product.

The fluid pathway connection assembly and drug container may be assembled in a number of methodologies. In one embodiment, the pierceable seal is inserted, at least partially, into the distal end of the drug container. A crimp cap is installed at the distal end of the drug container to securely constrain the pierceable seal to the drug container. The piercing member is assembled to the drug container such that the piercing member is, at least partially, disposed within the cavity of the pierceable seal. The fluid pathway assembly may also be in fluid communication with the needle insertion mechanism. After assembly, these components may be sterilized. Additionally, after assembly, the sleeve of the fluid pathway connection may be in sealing engagement with a portion of the pierceable seal to create a sterile volume within which a portion of the piercing member is disposed. The drug container may subsequently be filled with a medicament and a plunger seal placed within the drug container.

Manufacturing of a drug pump includes the step of attaching both the fluid pathway connection assembly and drug container, either separately or as a combined component, to an assembly platform or housing of the drug pump. The method of manufacturing further includes attachment of the drive mechanism, drug container, and insertion mechanism to the assembly platform or housing. The additional components of the drug pump, as described above, including the power and control system, the activation mechanism, and the control arm may be attached, preformed, or preassembled to the assembly platform or housing. An adhesive patch and patch liner may be attached to the housing surface of the drug pump that contacts the target during operation of the device.

A method of operating the drug pump includes the steps of: activating, by a user, the activation mechanism; displacing a control arm to actuate an insertion mechanism; actuating a fluid pathway connection assembly; and actuating a power and control system to activate a drive control mechanism to drive fluid drug flow through the drug pump, wherein actuating the fluid pathway connection assembly causes a piercing member to penetrate a pierceable seal thereby opening a fluid path from a drug container to the fluid pathway connection assembly. The method may further include the step of: engaging an optional on-body sensor prior to activating the activation mechanism. Furthermore, the method of operation may include translating a plunger seal within the drive control mechanism and drug container to force fluid drug flow through the drug container, the fluid pathway connection assembly, a sterile fluid conduit, and the insertion mechanism for delivery of the fluid drug to the target.

It will be appreciated that the foregoing description provides examples of the disclosed system and technique. However, it is contemplated that other implementations of the disclosure may differ in detail from the foregoing examples. All references to the disclosure or examples thereof are intended to reference the particular example being discussed at that point and are not intended to imply any limitation as to the scope of the disclosure more generally. All language of distinction and disparagement with respect to certain features is intended to indicate a lack of preference for those features, but not to exclude such from the scope of the disclosure entirely unless otherwise indicated.

While example embodiments have been particularly shown and described, it will be understood by those skilled in the art that various changes in form and details may be made therein without departing from the scope of the embodiments encompassed by the appended claims.

What is claimed is:

1. A fluid pathway connection assembly, comprising:
a hollow needle piercing member comprising a bent portion;
a sleeve fixedly engaged with the piercing member, the sleeve comprising a flange portion and an elongated portion, the bent portion of the piercing member disposed within the flange portion of the sleeve; and
a pierceable seal configured to sealingly engage the elongated portion of the sleeve, wherein:
in sealing engagement, the elongated portion of the sleeve and the pierceable seal form a volume within which a portion of the piercing member is disposed;
the fluid pathway connection assembly is activated by relative translation of the sleeve within the pierceable seal and activation causes the piercing member to pierce the pierceable seal, thereby establishing a fluid flowpath through the pierceable seal; and
upon incorporation of the assembly into a sealed fluid flowpath, the volume is isolated from the environment and maintains the sterile condition of the portion of the piercing member disposed therein.

2. The assembly of claim 1, wherein the hollow needle piercing member is a rigid, hollow needle.

3. The assembly of claim 1, wherein the sleeve includes side channels to facilitate sterilization.

4. The assembly of claim 1, wherein the pierceable seal includes one or more sealing ribs for sealingly engaging the piercing member or the sleeve.

5. The assembly of claim 1, wherein the pierceable seal includes a recess and a tip of the piercing member is disposed within the recess upon establishment of the fluid flowpath through the pierceable seal.

6. The assembly of claim 1, further comprising a retainer that restricts deformation of the pierceable seal or prevents inadvertent relative movement between the piercing member and the pierceable seal.

7. The assembly of claim 1, wherein one or more of the piercing member, the sleeve and the pierceable seal includes a vent which allows for evacuation of the volume.

8. The assembly of claim 1, further comprising a crimp cap for securing the pierceable seal to a drug container.

9. The assembly of claim 1, wherein the pierceable seal is configured to sealingly engage a drug container.

10. A drug delivery pump, comprising an assembly of claim 1.

11. A drug delivery pump comprising a pump housing including:
an activation mechanism;
a power and control system;
a drive mechanism including a drug container;
an insertion mechanism for delivering drug fluid to a target;
a fluid pathway connection assembly, comprising:
a hollow needle piercing member comprising a bent portion;
a sleeve fixedly engaged with the piercing member, the sleeve comprising a flange portion and an elongated portion, the bent portion of the piercing member disposed within the flange portion of the sleeve; and
a pierceable seal configured to sealingly engage the elongated portion of the sleeve and the drug container; and
a fluid conduit that fluidly connects the fluid pathway connection assembly to the insertion mechanism,
wherein:
in sealing engagement, the elongated portion of the sleeve and the pierceable seal form a volume within which a portion of the piercing member is disposed;
actuation of the activation mechanism initiates the power and control system, which activates the fluid pathway connection assembly, thereby establishing a fluid flowpath from the drug container through the fluid pathway connection assembly and the fluid conduit to the insertion mechanism, and the drive mechanism, thereby driving drug fluid through the fluid flowpath;
the fluid pathway connection assembly is activated by relative translation of the sleeve within the pierceable seal and activation causes the piercing member to pierce the pierceable seal, thereby establishing a fluid flowpath through the fluid pathway connection assembly; and
the volume is isolated from the environment and maintains the sterile condition of the portion of the piercing member disposed therein.

12. The drug delivery pump of claim 11, further comprising an on-body sensor.

13. The drug delivery pump of claim 11, wherein the drug container contains drug fluid.

14. A method of operating a drug delivery pump, the drug delivery pump comprising:
an activation mechanism;
a power and control system;
a drive mechanism including a drug container;
an insertion mechanism for delivering drug fluid to a target;
a fluid pathway connection assembly including a hollow needle piercing member comprising a bent portion, a sleeve fixedly engaged with the piercing member, the sleeve comprising a flange portion and an elongated portion, the bent portion of the piercing member disposed within the flange portion of the sleeve, and a pierceable seal configured to sealingly engage the the elongated portion of the sleeve and the drug container, wherein, in sealing engagement, the elongated portion of the sleeve and the pierceable seal form a volume within which a portion of the piercing member is disposed and which, upon incorporation of the assembly into a sealed fluid pathway, is isolated from the environment and maintains the sterile condition of the portion of the piercing member disposed therein; and
a fluid conduit that fluidly connects the fluid pathway connection assembly to the insertion mechanism, the method comprising:
activating the activation mechanism;
actuating the insertion mechanism;
actuating the fluid pathway connection assembly; and
initiating the power and control system to activate the drive mechanism to drive fluid drug through the drug delivery pump, wherein:
actuating the fluid pathway connection assembly, the actuating including causing relative transition of the sleeve within the pierceable seal and causing the piercing member to pierce the pierceable seal, thereby establishing a fluid flowpath from the drug container through the fluid pathway connection assembly and the fluid conduit to the insertion mechanism, thereby delivering fluid drug to the target.

15. A method of assembling a fluid pathway connection assembly and a drug container, comprising:

providing a fluid pathway connection assembly including a hollow needle piercing member comprising a bent portion, a sleeve comprising a flange portion and an elongated portion, and a pierceable seal configured to sealingly engage the elongated portion of the sleeve, the pierceable seal having a cavity;

inserting, at least partially, the pierceable seal into an end of a drug container;

securely constraining the pierceable seal to the drug container;

disposing, as least partially, the piercing member in the cavity of the pierceable seal;

fixedly securing the piercing member and the sleeve to one another, the bent portion of the piercing member disposed within the flange portion of the sleeve; and sealingly engaging the pierceable seal and the elongated portion of the sleeve, thereby forming a volume, wherein:

a portion of the piercing member is disposed within the volume, which, upon incorporation of the fluid pathway connection assembly into a sealed fluid flowpath, is isolated from the environment and maintains the sterile condition of the portion of the piercing member disposed therein; and the fluid pathway connection assembly is activated by relative translation of the sleeve within the pierceable seal and activation causes the piercing member to pierce the pierceable seal, thereby assembling the fluid connection pathway and the drug container.

* * * * *